United States Patent
Lee et al.

(10) Patent No.: US 8,969,600 B2
(45) Date of Patent: Mar. 3, 2015

(54) METHOD FOR PRODUCING GLYCIDOL

(71) Applicant: Korea Institute of Science and Technology, Seoul (KR)

(72) Inventors: Hyun Joo Lee, Gyeonggi-do (KR); Sang Deuk Lee, Seoul (KR); Byoung Sung Ahn, Seoul (KR); Chang Soo Kim, Daegu (KR); Ji Sik Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/759,692

(22) Filed: Feb. 5, 2013

(65) Prior Publication Data

US 2014/0135512 A1    May 15, 2014

(30) Foreign Application Priority Data

Nov. 14, 2012   (KR) .................. 10-2012-0128520

(51) Int. Cl.
*C07D 301/02*    (2006.01)

(52) U.S. Cl.
CPC .................................. *C07D 301/02* (2013.01)
USPC ....................................................... 549/518

(58) Field of Classification Search
CPC .................................................... C07D 301/02
USPC ....................................................... 549/518
See application file for complete search history.

(56) References Cited

U.S. PATENT DOCUMENTS 2,856,413 A * 10/1958 Malkemus et al. ............ 549/518
2011/0046401 A1 * 2/2011 Gumlich et al. .............. 549/518

FOREIGN PATENT DOCUMENTS

WO    WO 2009153194 A1 * 12/2009

OTHER PUBLICATIONS

Guo, Feng, et al. "One-step production of biodiesel from Jatropha oil with high-acid value in ionic liquids" 2011 [Bioresour. Technol. 102 (11): 6469-6472.*
Pearson, R.G., Hard and Soft Acids and Bases (1963), J. Am. Chem. Soc. 85(22): 3533-3539.*
Philip G. Jessop, et al; "Solvatochromic parameters for solvents of interest in green chemistry", Green Chem., vol. 14, pp. 1245-1259; First published online Mar. 20, 2012.
Ralf Lungwitz, et al; "A hydrogen bond accepting (HBA) scale for including room temperature ionic liquids", New Journal of Chemistry, vol. 32, pp. 392-394, First published online Jan. 24, 2008.
Lorna Crowhurst, et al; "Solvent-solute interactions in ionic liquids", Phy. Chem. Chem. Phys., vol. 5, pp. 2790-2794, First published as an Advance Article on the web May 29, 2003.
M.A.Ab Rani, et al; "Understanding the polarity of ionic liquids", Phys. Chem. Chem. Phys., vol. 13, pp. 16831-16840; First published online Aug. 22, 2011.
Swapna M. Gade, et al; "Synthesis of glycidol from glycerol and dimethyl carbonate using ionic liquid as a catalyst", Catalysis Communications, vol. 2, pp. 184-188, Available online Jul. 14, 2012.

* cited by examiner

*Primary Examiner* — Noble Jarrell
*Assistant Examiner* — John Mauro
(74) *Attorney, Agent, or Firm* — Ladas & Parry LLP

(57) ABSTRACT

Disclosed is a method for producing glycidol by decarboxylation of glycerol carbonate. In the method, an ionic liquid catalyst is added for the reaction. According to the method glycidol can be produced in high yield and selectivity. The method enables the production of glycidol in an easy, simple and environmentally friendly way.

9 Claims, 1 Drawing Sheet

METHOD FOR PRODUCING GLYCIDOL

CROSS-REFERENCE TO RELATED APPLICATIONS

This application claims priority under 35 U.S.C. §119 to Korean Patent Application No. 10-2012-0128520 filed on Nov. 14, 2012, in the Korean Intellectual Property Office, the disclosure of which is incorporated herein by reference in its entirety.

BACKGROUND OF THE INVENTION

1. Field of the Invention

The present invention relates to a method for producing glycidol by decarboxylation of glycerol carbonate.

2. Description of the Related Art

In recent years, there has been an increasing demand for and interest in biodiesel, which is synthesized from vegetable oils or animal fats, as a new renewable energy source. Biodiesel is produced by reaction of fatty acids with alcohols. Glycerol as a by-product accounts for about 10% by weight of the total biodiesel production. The price of glycerol is declining due to oversupply. One approach to convert cheap glycerol to high value-added products is thermal decomposition of glycerol carbonate as a glycerol derivative to synthesize glycidol. Glycidol is currently used in various applications, including cleaning agents in the petroleum industry, drug delivery materials, and raw materials for polymers. Glycidol is industrially produced by oxidation of allyl alcohol with hydrogen peroxide in the presence of a catalyst. However, this method involves a complicated process to purify glycidol despite its high production yield. Another disadvantage of the method is that a tungsten oxide compound as the catalyst tends to decompose during the reaction, resulting in an increase in the production cost of glycidol.

FIG. 1 shows a novel synthetic method for glycidol based on the thermal decomposition of glycerol carbonate. According to this method, the reaction proceeds in the presence of a metal salt catalyst. As a result of the reaction, glycidol as a product is produced along with carbon dioxide as a by-product. The carbon dioxide is reacted with ammonia to produce urea, which is then reacted with glycerol to synthesize glycerol carbonate as a raw material for glycidol. The method is associated with the production of glycidol by decarboxylation of glycerol carbonate derived from glycerol and is worthy of development from an economic and environmental viewpoint due to the use of the biomaterial-based raw material.

In this connection, U.S. Pat. No. 2,856,413 and Japanese Patent Publication No. Hei 6-157906 disclose methods for producing glycidol from glycerol carbonate using metal salts, such as $Na_3PO_4$, $CaCO_3$ and $Na_2SO_4$ as catalysts. Although these patent publications propose the use of various metal salt catalysts, they fail to mention approaches to inhibit side reactions.

Further, Japanese Patent Publication No. 2009-137938 and U.S. Pat. No. 6,316,641 disclose methods for synthesizing glycidol in high yield. According to these methods, the reaction may proceed in an active hydrogen-free solvent, such as an ether-based solvent, an aromatic hydrocarbon-based solvent or a saturated hydrocarbon-based solvent, in the presence of $Na_2SO_4$ or zeolite A as a catalyst, or the reaction may proceed using a thin-film reactor. The methods are effective in inhibiting side reactions to obtain glycidol in high yield, but the ability of the catalyst to inhibit side reactions is limited.

Similarly to the methods for producing glycidol from glycerol carbonate, methods for producing glycidol from glycerol and ethylene carbonate, propylene carbonate or butylene carbonate are disclosed in U.S. Pat. No. 2,636,040. According to these methods, glycidol is produced by gradually heating glycerol and an alkylene carbonate from 145° C. to 155-240° C. while decreasing the pressure from 75 mmHg to 10-15 mmHg in a distilled column to obtain glycerol carbonate as an intermediate, and distilling the intermediate at 11 mmHg and 80° C. However, a disadvantage of the methods is that reverse reactions are likely to occur in the course of obtaining the intermediate.

SUMMARY OF THE INVENTION

Therefore, the present invention is intended to provide a method for producing glycidol, which is used in a variety of industrial applications, by which glycidol can be produced in high yield and selectivity, and the production process can be carried out in an easy, simple and environmentally friendly way to create huge economic and environmental ripple effects.

According to an aspect of the present invention, there is provided a method for producing glycidol by decarboxylation of glycerol carbonate wherein an ionic liquid catalyst is added for the reaction.

In one embodiment of the present invention, the ionic liquid catalyst may have at least one cation selected from the group consisting of compounds represented by Formulae 1 to 3:

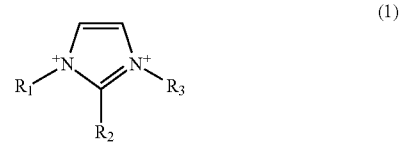

(1)

wherein $R_1$, $R_2$, and $R_3$ are independently H or a $C_1$-$C_6$ alkyl group;

(2)

wherein $R_1$, $R_2$, $R_3$, and $R_4$ are independently H or a $C_1$-$C_6$ alkyl group; and

(3)

wherein $R_1$ and $R_2$ are independently H or a $C_1$-$C_6$ alkyl group.

In a further embodiment of the present invention, the ionic liquid catalyst may have at least one anion selected from the group consisting of $PF_6^-$, $BF_4^-$, $F_3CSO_3^-$, $NO_3^-$, $I^-$, $Br^-$, $Cl^-$, $CH_3CO_2^-$, and $HCO_3^-$.

In another embodiment of the present invention, the anion of the ionic liquid catalyst may have a β value, which is the Kamlet-Taft parameter representing basicity, in the range of 0.60 to 0.80.

In another embodiment of the present invention, the ionic liquid catalyst may be used in an amount of 0.0025 moles or less per one mole of the glycerol carbonate.

In another embodiment of the present invention, a Lewis acid metal salt, together with the ionic liquid catalyst, may be further added.

In another embodiment of the present invention, the Lewis acid metal salt may be selected from the group consisting of $Zn(NO_3)_2$, $ZnCl_2$, $SnCl_4$, $MgCl_2$, $AlCl_3$, and mixtures thereof.

In another embodiment of the present invention, the Lewis acid metal salt may be added in an amount of 0.2 moles or less per one mole of the ionic liquid catalyst.

In another embodiment of the present invention, the decarboxylation may be carried out at a temperature not higher than 175° C. for a time shorter than 30 minutes.

In another embodiment of the present invention the decarboxylation may be carried out in a continuous reaction to continuously collect glycidol as the product.

According to the method of the present invention, glycidol can be produced in high yield and selectivity. In addition, the method of the present invention enables the production of glycidol in an easy, simple and environmentally friendly way.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail. The present inventors have found that the addition of an ionic liquid catalyst during decarboxylation of glycerol carbonate can markedly improve the production yield of glycidol(2,3-epoxy-1-propanol) and the selectivity to glycidol. The present invention has been achieved based on this finding. The production yield of glycidol is varied depending on the hydrogen bond basicity of the anion of the ionic liquid, as can be seen from the Examples Section that follows. The use of catalysts having anions whose hydrogen bond basicities are intermediate leads to higher yields of glycidol than the use of catalysts having anions whose hydrogen bond basicities are too low or high. Furthermore, when a Lewis acid metal salt is added in an optimum amount simultaneously with addition of the ionic liquid catalyst and the reaction is carried out in a continuous manner, glycidol can be produced in higher yield.

Figure 1:
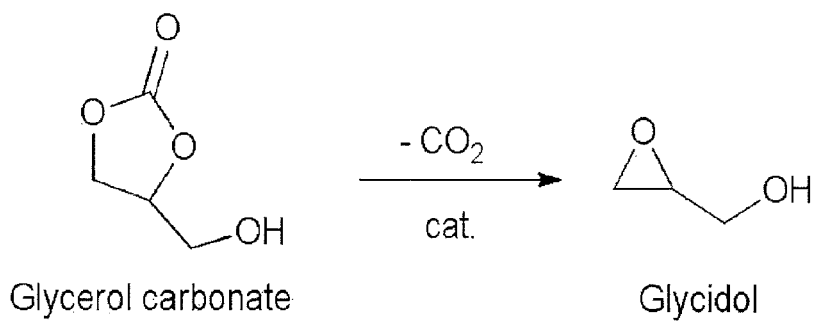
FIG. 1 is a reaction schematically showing the production of glycidol by decarboxylation of glycerol carbonate.

In view of the foregoing, the present invention provides a method for producing glycidol by decarboxylation of glycerol carbonate wherein an ionic liquid catalyst is added for the reaction. According to the method of the present invention, glycidol is synthesized by direct decarboxylation of glycerol carbonate (GLC) in the presence of an ionic liquid catalyst. The reaction is shown in FIG. 1.

The ionic liquid catalyst may be an ionic compound consisting of at least one cation selected from the group consisting of compounds represented by Formulae 1 to 3:

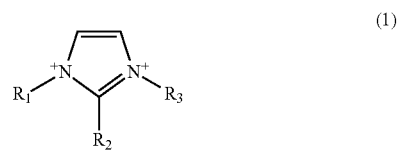

wherein $R_1$, $R_2$, and $R_3$ are independently H or a $C_1$-$C_6$ alkyl group;

wherein $R_1$, $R_2$, $R_3$, and $R_4$ are independently H or a $C_1$-$C_6$ alkyl group; and

wherein $R_1$ and $R_2$ are independently H or a $C_1$-$C_6$ alkyl group, and at least one anion selected from the group consisting of $PF_6^-$, $BF_4^-$, $F_3CSO_3^-$, $NO_3^-$, F, Br$^-$, Cl$^-$, $CH_3CO_2^-$, and $HCO_3^-$.

Particularly, the anions of the ionic liquid catalyst interact with GLC as the reactant and glycidol as the product through the hydroxyl groups thereof. This degree of interaction is greatly influenced by the hydrogen bond basicity of the anions of the ionic liquid catalyst. The hydrogen bond basicity can be quantified by a β value reported as the Kamlet-Taft solvent parameter, and a description thereof can be found in many publications, for example: P. G. Jessop, D. A. Jessop, D. Fu, L. Phan, Green Chem. 14 (2012) 1245; R. Lungwitx, S. Spange, New J. Chem. 32 (2008) 392; L. Crowhurst, P. R. Mawdsley, J. M. Perez-Arlandis, P. A. Salter. T. Welton, Phys. Chem. Chem. Phys. 5 (2003) 2790; and M. A. A. Rani, A. Brant, L. Crowhurst, A. Dolan. M. Lui, N. H. Hassan, J. P. Hallett, P. A. Hunt, H. Niedermeyer, J. M. Perez-Arlandis, M. Schrems, T. Welton, R. Wilding, Phys. Chem. Chem. Phys. 13 (2011) 16831. The β value of the ionic liquid catalyst used in the method of the present invention is preferably from 0.60 to 0.80. If the β value is out of the range defined above, the yield of glycidol and the selectivity to glycidol are considerably lowered, as can be seen from the results of the Examples Section that follows. A specific, non-limiting example of the ionic liquid catalyst meeting the above requirement is 1-butyl-3-methylimidazolium nitrate.

The molar ratio of glycerol carbonate as the reactant to the ionic liquid catalyst affects the yield of glycidol. The use of the ionic liquid catalyst whose β value is within the range (from 0.60 to 0.80) defined above gradually increases the production yield of glycidol with increasing amount of the catalyst, and the addition of the catalyst in an amount above a particular value does not lead to a reduction in the yield of glycidol. In contrast, the use of the ionic liquid catalyst whose (3 value is outside the range defined above in an amount of up to about 0.0025 moles per one mole of glycerol carbonate gradually increases the yield of glycidol with increasing amount of the catalyst, but the use of the ionic liquid catalyst in an excess amount leads to the production of dimers and polymers as by-products, indicating low yield of the product.

To further improve the production yield of glycidol, a Lewis acid metal salt may be further added along with the ionic liquid catalyst. The reason for the addition of the Lewis acid metal salt is that the Lewis acid metal salt controls the basicity of the reaction solution to effectively inhibit the occurrence of side reactions. Specifically, the Lewis acid metal salt is selected from the group consisting of $Zn(NO_3)_2$, $ZnCl_2$, $SnCl_4$, $MgCl_2$, $AlCl_3$, and mixtures thereof.

The amount of the Lewis acid metal salt relative to that of the ionic liquid catalyst also affects the production yield of glycidol. It is preferred to add the Lewis acid metal salt catalyst in an amount of 0.2 moles or less per one mole of the ionic liquid catalyst. Specifically, the yield of glycidol is gradually increased with increasing amount of the Lewis acid metal salt to 0.2 moles per one mole of the ionic liquid catalyst but is slightly decreased when the Lewis acid metal salt is used in an amount exceeding 0.2 moles, as can be seen from the Examples Section that follows.

In the method of the present invention, the decarboxylation is preferably carried out at a temperature not higher than 175° C. for a time shorter than 30 minutes. As a result of experiments, the yield of glycidol is increased with rising temperature and reached a maximum at about 175° C., but the selectivity to glycidol is decreased at a temperature higher than 175° C. According to the present invention, the reaction of the catalytic reaction system is allowed to proceed very rapidly and is completed after about 30 minutes.

Particularly, as the decarboxylation proceeds in the method of the present invention, glycidol is produced, and at the same time, the catalyst is highly concentrated in a reactor, which increases the risk of side reactions. For the purpose of effectively inhibiting the occurrence of side reactions, the decarboxylation is preferably carried out in a continuous reaction to continuously collect glycidol as the product.

Figure 2:
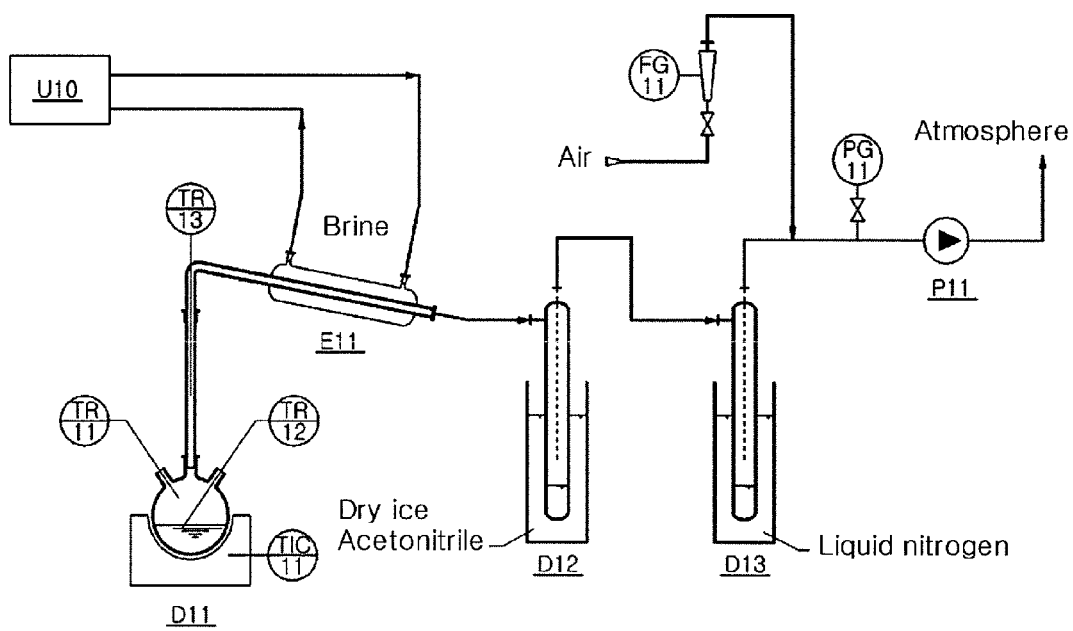
FIG. 2 is a schematic diagram showing a system for implementing a method of the present invention.

FIG. 2 schematically shows a system for implementing a method according to one embodiment of the present invention. As shown in FIG. 2, the system includes a reactor D11 equipped with a heating mantle for heating the reactant, a condenser E11 for condensing vapor released as a result of the reaction in the reactor D11, a brine circulator U10 adapted to supply a coolant to the condenser E11, a product receiver D12 for accommodating a condensate from the condenser E11, a cooling collector D13 cooled by liquid nitrogen to collect an uncondensed component from the product receiver D12, and a vacuum pump P11 for depressurization. The system further includes temperature recorders TR-11, TR-12 and TR-13, a temperature indicator controller TIC-11 for controlling the temperature of the reactor D11, a pressure gauge PG-11 for system pressure measurement, a flow gauge FG-11 for vacuum control, etc.

The present invention will be explained in more detail with reference to the following examples. However, these examples are given to assist the understanding of the invention and are not intended to limit the scope of the invention.

EXAMPLES

Example 1

18.14 g (154 mmol) of glycerol carbonate, 0.15 g (0.74 mmol) of 1-butyl-3-methylimidazolium nitrate as an ionic liquid catalyst, and 0.03 g (0.15 mmol) of $Zn(NO_3)_2$ as a Lewis acid metal salt were put in a 100 mL three-neck flask. The mixture was slowly heated to 175° C. with stirring at ambient pressure. When the temperature reached 175° C., the mixture was depressurized to 2.67 kPa and was then allowed to react for 45 min. After completion of the reaction, t-butanol and DMSO were added as internal standards for HPLC and GC analyses of the reactant and the product, respectively. As a result, the yield of glycidol and the selectivity to glycidol were 77.2% and 78.0%, respectively.

Examples 2-10

Glycidol was synthesized in the same manner as in Example 1, except that the kind of the anion of the ionic liquid was changed as shown in Table 1. The ionic liquids had the same cation (i.e. 1-butyl-3-methylimidazolium). The results are shown in Table 1.

TABLE 1

| Example No. | Catalyst | Conversion (%) | Yield (%) | Selectivity (%) | Basicity (β) |
|---|---|---|---|---|---|
| 2 | — | 4.5 | 3.4 | — | — |
| 3 | [BMIm]$PF_6$ | 4.3 | 1.2 | 26.1 | 0.29 |
| 4 | [BMIm]$BF_4$ | 4.7 | 2.0 | 42.6 | 0.36 |
| 5 | [BMIm]OTf | 29.6 | 14.6 | 54.6 | 0.49 |
| 6 | [BMIm]$NO_3$ | 99.8 | 68.7 | 68.9 | 0.56 |
| 7 | [BMIm]I | 98.2 | 69.8 | 71.0 | 0.75 |
| 8 | [BMIm]Br | 93.8 | 60.2 | 64.3 | 0.87 |
| 9 | [BMIm]Cl | 99.8 | 57.1 | 57.3 | 0.93 |
| 10 | [BMIm]$CH_3CO_2$ | 99.4 | 39.3 | 39.6 | 0.99 |

For better understanding of the effect of the anions on the decarboxylation of GLC, the concept of hydrogen bond basicities (β values) of the ionic liquids and the Kamlet-Taft solvent parameters determined by the anionic characteristics of the ionic liquids were introduced. As a result of comparing the correlations between the reported β values of the ionic liquids and the yields of glycidol in Examples 2-10, the yield of glycidol increased with increasing β value to 0.80, and thereafter began to decrease. The use of the ionic liquids whose β values were from 0.60 to 0.80 gave higher glycidol yields than the use of the ionic liquids whose β values were more than 0.80 or less than 0.60. In contrast to this, when the ionic liquids having β values of 0.60 or more were used, the conversions of GLC were maintained at almost 95% or more. These results demonstrate that the ionic liquids have better activity and selectivity when the β values of the anions are preferably in the range of 0.60 to 0.80.

Examples 11-14

Glycidol was synthesized in the same manner as in Example 1, except that the kind of the cation of the ionic liquid was changed as shown in Table 2 and the Lewis acid metal salt $Zn(NO_3)_2$ was not added. The ionic liquids had the same anion (i.e. $NO_3^-$). The results are shown in Table 2.

TABLE 2

| Example No. | Catalyst | Conversion (%) | Yield (%) | Selectivity (%) |
|---|---|---|---|---|
| 11 | [BMIm]$NO_3$ | 99.8 | 68.7 | 68.9 |
| 12 | [BDMIm]$NO_3$ | 99.1 | 73.2 | 73.9 |
| 13 | [$Bu_4$N]$NO_3$ | 99.3 | 64.2 | 63.8 |
| 14 | [MPPyr]$NO_3$ | 100.0 | 58.9 | 58.9 |

Examples 15-20

The synthesis yields of glycidol depending on the molar ratio of [BMIm]NO$_3$ as an ionic liquid catalyst to glycerol carbonate were compared. For this comparison, glycidol was synthesized in the same manner as in Example 1, except that the amount of [BMIm]NO$_3$ was changed as shown in Table 3 and the Lewis acid metal salt Zn(NO$_3$)$_2$ was not added. The results are shown in Table 3.

TABLE 3

| Example No. | Molar ratio of [BMIm]NO$_3$/GLC | Conversion (%) | Yield (%) | Selectivity (%) |
|---|---|---|---|---|
| 2 | 0 | 4.5 | 3.4 | — |
| 15 | 0.00125 | 82.3 | 57.2 | 69.5 |
| 16 | 0.0025 | 96.8 | 69.1 | 71.3 |
| 17 | 0.00375 | 98.2 | 68.8 | 70.1 |
| 18 | 0.005 | 99.8 | 68.7 | 68.9 |
| 19 | 0.01 | 100 | 69 | 69 |
| 20 | 0.02 | 100 | 68.8 | 68.8 |

As can be seen from the results in Table 3, the conversion to GLC reached 82.3% even when the catalyst was present in a small amount. The yield of glycidol was gradually increased until the molar ratio of [BMIm]NO$_3$/GLC reached 0.0025 and thereafter it was maintained almost constant even when the molar ratio was increased above 0.0025.

Examples 21-32

The synthesis yields of glycidol depending on the molar ratio of [BMIm]NO$_3$ as an ionic liquid catalyst to Zn(NO$_3$)$_2$ as a Lewis acid metal salt were compared. For this comparison, glycidol was synthesized in the same manner as in Example 1, except that the moles of [BMIm]NO$_3$ and Zn(NO$_3$)$_2$ were changed as shown in Table 4. The results are shown in Table 4.

TABLE 4

| | Number of moles | | | | |
|---|---|---|---|---|---|
| Example No. | Glycerol carbonate | [BMIm]NO$_3$ | Zu(NO$_3$)$_2$ | Yield (%) | Selectivity (%) |
| 21 | 1 | 0.5 | 0.05 | 71.9 | 72.7 |
| 1 | 1 | 0.5 | 0.1 | 77.2 | 78.0 |
| 22 | 1 | 0.5 | 0.25 | 74.9 | 74.9 |
| 23 | 1 | 0.5 | 0.5 | 72.9 | 73.3 |
| 24 | 1 | 0.5 | 1 | 71.9 | 72.9 |
| 25 | 1 | 0.05 | 0.5 | 55.3 | 71.5 |
| 26 | 1 | 0.1 | 0.5 | 57.2 | 69.5 |
| 27 | 1 | 0.25 | 0.5 | 65.0 | 65.2 |
| 28 | 1 | 1 | 0.5 | 73.6 | 76.4 |
| 29 | 1 | 0.125 | 0.0625 | 59.8 | 73.7 |
| 30 | 1 | 0.25 | 0.125 | 74.7 | 78.7 |
| 31 | 1 | 0.375 | 0.1875 | 71.8 | 77.2 |
| 32 | 1 | 2 | 1 | 64.8 | 64.8 |

As can be seen from the results in Table 4, the addition of Zn(NO$_3$)$_2$ was effective in increasing the yield of glycidol while inhibiting side reactions and the effect was maximized when Zn(NO$_3$)$_2$ was added in an amount of 0.2 moles per one mole of the catalyst [BMIm]NO$_3$.

Examples 33-36

The synthesis yields of glycidol when metal salts other than the zinc salt were used as Lewis acid metal salts were compared. For this comparison, glycidol was synthesized in the same manner as in Example 1, except that other Lewis acid metal salts were added to the catalyst [BMIm]NO$_3$ instead of Zn(NO$_3$)$_2$. The results are shown in Table 5.

TABLE 5

| Example No. | Catalyst added | Conversion (%) | Yield (%) | Selectivity (%) |
|---|---|---|---|---|
| 1 | Zn(NO$_3$)$_2$ | 99.0 | 77.2 | 78.0 |
| 33 | ZnCl$_2$ | 97.5 | 74.3 | 76.2 |
| 34 | SnCl$_4$ | 99.8 | 53.2 | 58.4 |
| 35 | MgCl$_2$ | 99.4 | 74.5 | 74.9 |
| 36 | AlCl$_3$ | 99.9 | 73.8 | 73.9 |

As can be seen from the results in Table 5, ZnCl$_2$, MgCl$_2$, AlCl$_3$ were also observed to have similar effects to Zn(NO$_3$)$_2$, but SnCl$_4$ failed to show a good yield of glycidol. This phenomenon indicates that effects of adding the Lewis acids may vary depending on the kind and/or strength of the metal salts.

Examples 37-45

The synthesis yields of glycidol depending on processing conditions were compared. For this comparison, glycidol was synthesized in the same manner as in Example 1, except that the reaction temperature, time and pressure were changed as shown in Table 6. The results are shown in Table 6.

TABLE 6

| | Reaction conditions | | | | |
|---|---|---|---|---|---|
| Example No. | Temperature (° C.) | Time (min) | Pressure (mmHg) | Yield (%) | Selectivity (%) |
| 37 | 140 | 45 | 20 | — | — |
| 38 | 165 | 45 | 20 | 31.4 | 68.9 |
| 1 | 175 | 45 | 20 | 77.2 | 78.0 |
| 39 | 185 | 45 | 20 | 65.6 | 65.6 |
| 40 | 175 | 10 | 20 | 6.6 | 20.0 |
| 41 | 175 | 20 | 20 | 51.6 | 78.4 |
| 42 | 175 | 30 | 20 | 75.3 | 76.0 |
| 43 | 175 | 60 | 20 | 73.0 | 73.1 |
| 44 | 175 | 45 | 70 | 44.4 | 45.0 |
| 45 | 175 | 45 | <10 | 58.5 | 77.9 |

Examples 46-51

For the purpose of obtaining higher selectivity to glycidol, high boiling point solvents were used and glycerol carbonate (GLC) was continuously fed to produce glycidol. Specifically, a high boiling point solvent (50 g), [BMIm]NO$_3$ (0.13 g), and Zn(NO$_3$)$_2$ (0.025 g) were placed in a 250 mL three-neck flask, and then the mixture was heated to 175° C. at 2.67 kPa. Subsequently, GLC was introduced into the flask at a flow rate of 0.2 mL/min using an HPLC pump over 2 hr. The resulting mixture was allowed to further react at the same temperature for 30 min. Polyethylene glycol dimethyl ether (DMPEG, Mw=350, 50 g), dibenzyl ether (50 g), and dibutyl phthalate (50 g) were used as high boiling point solvents. The effects of the solvents on the reactions were compared and the results are shown in Table 7.

TABLE 7

| Example No. | Solvent | Conversion (%) | Yield (%) | Selectivity (%) |
|---|---|---|---|---|
| 46 | DMPEG[a] | 99.7 | 83.2 | 83.5 |
| 47 | DMPEG[b] | 100 | 98.2 | 98.2 |

TABLE 7-continued

| Example No. | Solvent | Conversion (%) | Yield (%) | Selectivity (%) |
|---|---|---|---|---|
| 48 | Dibenzyl ether[a] | 100 | 82.1 | 82.1 |
| 49 | Dibenzyl ether[b] | 99.4 | 97.3 | 97.9 |
| 50 | Dibutyl phthalate[a] | 99.8 | 84.4 | 84.6 |
| 51 | Dibutyl phthalate[b] | 100 | 96.9 | 96.9 |

[a]Batch reaction using solvent
[b]Continuous reaction using solvent

As can be seen from the results in Table 7, glycidol was produced in higher conversion, yield and selectivity when GLC as the reactant was fed in a continuous reaction to continuously collect glycidol as the product rather than in a batch reaction.

Examples 52-60

The procedure of Example 47 was repeated 10 times to confirm the life of the catalyst. After 2.5 hr, the reactions were stopped and the yields of glycidol were analyzed. Thereafter, GLC was newly fed into each of the reaction flasks containing the solvent and the catalyst. This procedure was repeated 10 times. The results are shown in Table 8.

TABLE 8

| Example No. | Number of repeats | Yield (%) |
|---|---|---|
| 47 | 1 | 98.2 |
| 52 | 2 | 98.3 |
| 53 | 3 | 99.1 |
| 54 | 4 | 98.5 |
| 55 | 5 | 98.7 |
| 56 | 6 | 98.1 |
| 57 | 7 | 97.2 |
| 58 | 8 | 96.7 |
| 59 | 9 | 95.4 |
| 60 | 10 | 92.3 |

As can be seen from the results in Table 8, glycidol was produced in high yields even after many repeats.

What is claimed is:

1. A method for producing glycidol by decarboxylation of glycerol carbonate, wherein an ionic liquid catalyst is added for the reaction, wherein the ionic liquid catalyst comprises:

Formula 1

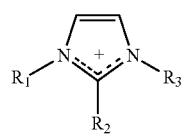
(1)

wherein $R_1$, $R_2$, and $R_3$ are independently H or a $C_1$-$C_6$ alkyl group;

Formula 2

(2)

wherein R1, R2, R3, and R4 are independently H or a C1-C6 alkyl group; and

Formula 3:

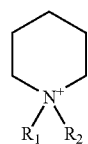
(3)

wherein $R_1$ and $R_2$ are independently H or a $C_1$-$C_6$ alkyl group.

2. The method according to claim 1, wherein the ionic liquid catalyst comprises at least one anion selected from the group consisting of $PF_6^-$, $BF_4^-$, $F_3CSO_3^-$, $NO_3^-$, $I^-$, $Br^-$, $Cl^-$, $CH_3CO_2^-$, and $HCO_3^-$.

3. The method according to claim 1, wherein the ionic liquid catalyst is used in an amount of 0.0025 moles or less per one mole of the glycerol carbonate.

4. The method according to claim 1, wherein a Lewis acid metal salt, together with the ionic liquid catalyst, is further added.

5. The method according to claim 4, wherein the Lewis acid metal salt is selected from the group consisting of $Zn(NO_3)_2$, $ZnCl_2$, $SnCl_4$, $MgCl_2$, $AlCl_3$, and mixtures thereof.

6. The method according to claim 4, wherein the Lewis acid metal salt is added in an amount of 0.2 moles or less per one mole of the ionic liquid catalyst.

7. The method according to claim 1, wherein a solvent is further added in which the solvent is selected from the group consisting of polyethylene glycol dimethyl ether (DMPEG), dibenzyl ether, and dibutylphthalate.

8. The method according to claim 1, wherein the decarboxylation and glycidol collection are carried out simultaneously in a continuous process.

9. A method for producing glycidol comprising:
putting together glycerol carbonate, 1-butyl-3-methylimidazolium nitrate, $Zn(NO_3)_2$, and a solvent to form a mixture, wherein the solvent is selected from the group consisting of polyethylene glycol dimethyl ether (DMPEG), dibenzyl ether, and dibutylphthalate;
heating the mixture to not higher than 175° C. at ambient pressure; and
depressurizing the heated mixture to produce glycidol.

* * * * *